US00PP15979P2

(12) United States Plant Patent
Bell

(10) Patent No.: US PP15,979 P2
(45) Date of Patent: Sep. 20, 2005

(54) ***COREOPSIS* PLANT NAMED 'LIMEROCK PASSION'**

(50) Latin Name: *Coreopsis hybrida*
Varietal Denomination: Limerock Passion

(75) Inventor: John Bell, Lancaster, PA (US)

(73) Assignee: Limerock Plant Farm, Inc., Lincoln, RI (US)

( * ) Notice: Subject to any disclaimer, the term of this patent is extended or adjusted under 35 U.S.C. 154(b) by 20 days.

(21) Appl. No.: 10/917,153

(22) Filed: Aug. 12, 2004

(51) Int. Cl.[7] ..... A01H 5/00
(52) U.S. Cl. ..... Plt./263
(58) Field of Search ..... Plt./263

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Coreopsis* plant named 'Limerock Passion', characterized by its daisy-type inflorescences; unique light red purple-colored ray florets and dark purple-colored disc florets; very freely flowering habit with numerous inflorescences per plant; and upright and outwardly spreading growth habit.

1 Drawing Sheet

Botanical classification/cultivar designation: *Coreopsis hybrida* cultivar Limerock Passion.

BACKGROUND OF THE INVENTION

The present invention relates to a new and distinct cultivar of *Coreopsis* plant, botanically known as *Coreopsis hybrida* and hereinafter referred to by the name 'Limerock Passion'.

The new *Coreopsis* was discovered and selected by the Inventor in a controlled environment in Lancaster, Pa. on Sep. 11, 2001, as a naturally-occurring branch mutation of the *Coreopsis hybrida* cultivar Limerock Ruby, disclosed in U.S. Plant Pat. No. 15,455. The branch mutation was observed by the Inventor within a population of flowering plants of the cultivar Limerock Ruby.

Asexual reproduction of the new *Coreopsis* by vegetative tip cuttings in a controlled environment in Smoketown, Pa., since Jan. 16, 2002, has shown that the unique features of this new *Coreopsis* are stable and reproduced true to type in successive generations.

SUMMARY OF THE INVENTION

The cultivar Limerock Passion has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Limerock Passion'. These characteristics in combination distinguish 'Limerock Passion' as a new and distinct cultivar:

1. Daisy-type inflorescences that are about 3.5 cm in diameter.
2. Unique light red purple-colored ray florets and dark purple-colored disc florets.
3. Very freely flowering with numerous inflorescences per plant.
4. Upright and outwardly spreading growth habit.

Plants of the new *Coreopis* are most similar to plants of the parent, the cultivar Limerock Ruby. In side-by-side comparisons conducted in Smoketown, Pa., plants of the new *Coreopsis* differed primarily from plants of the cultivar Limerock Ruby in ray floret coloration. Plants of various selections and other cultivars of *Coreopsis* known to the Inventor, not patented, also differ from plants of the new *Coreopsis* in ray floret coloration.

BRIEF DESCRIPTION OF THE PHOTOGRAPHS

The accompanying colored photographs illustrate the overall appearance of the new *Coreopsis*, showing the colors as true as it is reasonably possible to obtain in colored reproductions of this type. Colors in the photographs may differ slightly from the color values cited in the detailed botanical description which accurately describe the colors of the new *Coreopsis*.

The photograph at the top of the sheet comprises a side perspective view of a typical flowering plant of 'Limerock Passion'.

The photograph at the bottom of the sheet is a close-up view of typical inflorescences of 'Limerock Passion'.

DETAILED BOTANICAL DESCRIPTION

In the following description, color references are made to The Royal Horticultural Society Colour Chart, 1995 Edition, except where general terms of ordinary dictionary significance are used. The following observations and measurements describe pinched plants grown in Tolar, Tex. during the summer and fall outdoors under full sun and cultural conditions which approximate commercial practice. Plants used for the photographs and description were grown as single plants in one-gallon containers and were about nine months old. Measurements and numerical values represent averages taken from a group of flowering plants.

Botanical classification: *Coreopsis hybrida* cultivar Limerock Passion.

Parentage: Naturally-occurring branch mutation of *Coreopsis hybrida*, disclosed in U.S. Plant patent application Ser. No. 09/968,336.

Propagation:

*Type.*—Vegetative tip cuttings.

*Time to initiate roots.*—Summer: About 15 days at temperatures of 18° C. Winter: About 20 days at temperatures of 13° C.

*Time to produce a rooted cutting.*—About 36 days at temperatures of 18° C.

*Root description.*—Fine; well-branched.

Plant description:

*Appearance.*—Perennial; upright and outwardly spreading; mounding habit.

*Plant size.*—Height: About 35 cm. Diameter or spread: About 42 cm.

*Lateral branch description.*—Freely branching, usually two laterals will develop at every node. Pinching is not required, however plants tend to be sturdier and more upright if pinched. Aspect: Initially upright, then outwardly arching. Strength: Moderate; stems will start to arch outwardly with the weight of inflorescences. Length: About 34 cm. Diameter: About 2.2 mm. Internode length: About 3.75 cm. Texture: Smooth, glabrous. Color: Close to 146A.

*Foliage description.*—Arrangement: Opposite, single; sessile. Length: About 4.1 cm. Width: About 2.75 mm. Shape: Linear. Apex: Acute. Base: Attenuate. Texture, upper and lower surfaces: Smooth, glabrous. Color: Developing and fully expanded foliage, upper surface: Close to 147A; venation, similar to lamina. Developing and fully expanded foliage, lower surface: Close to 147B; venation, similar to lamina.

Flowering description:

*Appearance.*—Daisy-type inflorescence form with elongated oblong-shaped ray florets. Inflorescences borne on terminals, arising from leaf axils. Disc and ray florets develop acropetally on a capitulum. Inflorescences persistent.

*Flowering response.*—Under natural conditions, plant flower in the late spring after sufficient cool temperatures and continue to flower through the fall.

*Inflorescence longevity.*—Individual inflorescences last about one to two weeks.

*Quantity of inflorescences.*—Very freely flowering with more than 100 inflorescence buds and inflorescences per plant.

*Inflorescence size.*—Diameter: About 3.5 cm. Depth (height): About 9 mm. Diameter of disc: About 9 mm.

*Fragrance.*—Very faint; sweet, grass-like.

*Inflorescence buds.*—Height: About 5 mm. Diameter: About 5 mm. Shape: Roughly spherical. Color: Close to 172A; towards the base, close to 144A.

*Ray florets.*—Shape: Elongated oblong. Length: About 1.7 cm. Width: About 8 mm. Apex: Emarginate; deeply incised; jagged appearance. Base: Attenuate. Corolla tube length: About 3 mm. Margin: Entire. Texture: Smooth, glabrous; satiny. Aspect: Initially upright; with development, perpendicular to the peduncle. Initially concave, with development, mostly flat. Number of ray florets per inflorescence: About eight arranged in a single whorl. Color: When opening and fully opened, upper surface: Close to 155D overlain with 71A to 71A; light red purple coloration fading with development and becoming closer to light pink to white. When opening and fully opened, lower surface: Close to 155D underlain with 77A to 78A.

*Disc florets.*—Arrangement: Massed at the center of the inflorescence. Shape: Tubular, flared at apex. Length: About 3.5 mm. Width: Apex: About 2 mm. Base: About 1 mm. Number of disc florets per inflorescence: About 42. Color: Immature and mature: Apex: Close to 187B. Mid-section: Close to 9A. Base: Close to 155D.

*Involucral bracts.*—Quantity: About eight arranged in a single whorl. Length: About 5.75 mm. Width: About 2.75 mm at the base. Shape: Roughly ovate. Apex: Acute. Base: Truncate. Texture, upper and lower surfaces: Smooth, glabrous; waxy. Color, upper and lower surfaces: Close to 172A; towards the base, close to 144A.

*Peduncle.*—Strength: Very strong, wiry; flexible. Aspect: Mostly upright. Length: About 5.5 cm. Diameter: About 1 mm. Texture: Smooth, glabrous. Color: Close to 146A.

*Reproductive organs.*—Androecium: Present on disc florets only. Stamen quantity: Five per floret. Anther length: About 1.5 mm. Anther color: More brown than 187A. Amount of pollen: Moderate. Pollen color: 17A. Gynoecium: Present on disc florets only. Pistil quantity: One per floret. Pistil length: About 5 mm. Stigma shape: Bi-parted. Stigma color: Close to 17A. Style color: Close to 9A.

*Seed/fruit.*—Seed/fruit production has not been observed.

Disease/pest resistance: Resistance to pathogens and pests common to *Coreopsis* has not been observed on plants grown under commercial conditions.

Temperature tolerance: Plants of the new *Coreopsis* have demonstrated good tolerance to night temperatures as low as −5° C. and day temperatures as high as 42° C.

It is claimed:

1. A new and distinct cultivar of *Coreopsis* plant named 'Limerock Passion', as illustrated and described.

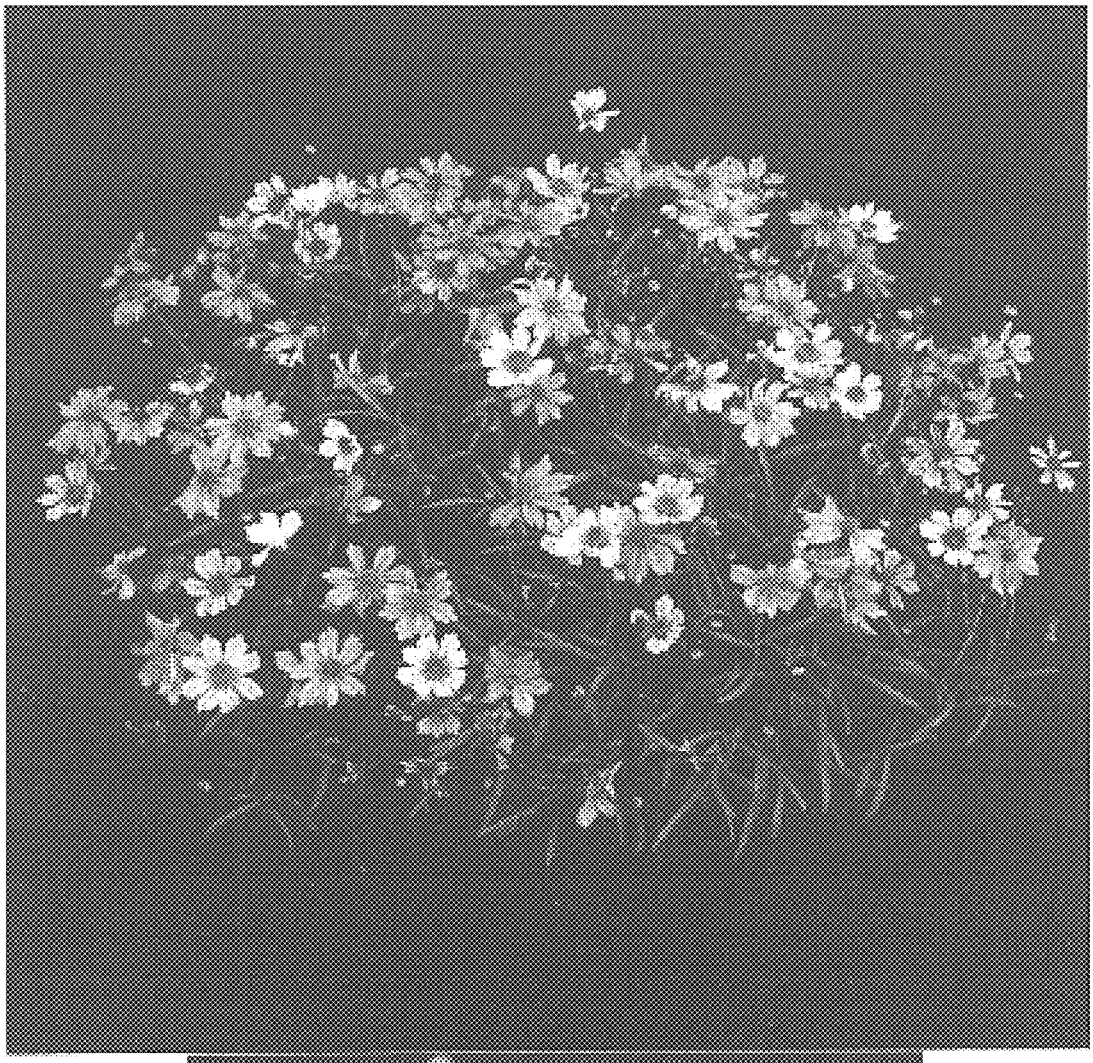
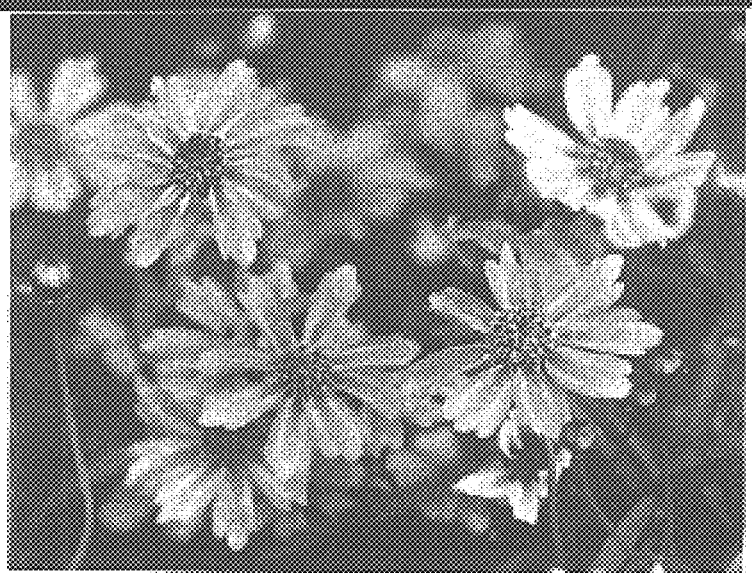

* * * * *